(12) United States Patent
Toporek

(10) Patent No.: US 12,011,573 B2
(45) Date of Patent: Jun. 18, 2024

(54) TOUCH SENSITIVE LABEL FOR AN INJECTION DEVICE

(71) Applicant: SANOFI, Paris (FR)

(72) Inventor: Maurice Toporek, Frankfurt am Main (DE)

(73) Assignee: Sanofi, Paris (FR)

( * ) Notice: Subject to any disclaimer, the term of this patent is extended or adjusted under 35 U.S.C. 154(b) by 789 days.

(21) Appl. No.: 17/043,554

(22) PCT Filed: May 16, 2019

(86) PCT No.: PCT/EP2019/062579
§ 371 (c)(1),
(2) Date: Sep. 29, 2020

(87) PCT Pub. No.: WO2019/219797
PCT Pub. Date: Nov. 21, 2019

(65) Prior Publication Data
US 2021/0106764 A1  Apr. 15, 2021

(30) Foreign Application Priority Data

May 17, 2018 (EP) .................................... 18305608

(51) Int. Cl.
*A61M 5/315* (2006.01)
*A61M 5/31* (2006.01)

(52) U.S. Cl.
CPC .... *A61M 5/31546* (2013.01); *A61M 5/31566* (2013.01); *A61M 2005/3125* (2013.01);
(Continued)

(58) Field of Classification Search
None
See application file for complete search history.

(56) References Cited

U.S. PATENT DOCUMENTS 4,718,896 A * 1/1988 Arndt .................. A61M 5/1689
D24/129
2008/0059133 A1  3/2008  Edwards et al.
(Continued)

FOREIGN PATENT DOCUMENTS

| CN | 102014992 | 4/2011 |
|---|---|---|
| CN | 104220116 | 12/2014 |

(Continued)

OTHER PUBLICATIONS

Translation of cited prior art JP 2016-512966A [Japanese to English]. (Year: 2016).*

(Continued)

*Primary Examiner* — Manuel A Mendez
(74) *Attorney, Agent, or Firm* — Fish & Richardson P.C.

(57) ABSTRACT

The present disclosure relates to a touch sensitive label for an injection device, the label comprising: a flexible substrate configured for attachment to a housing of the injection device, an electronic display located on the substrate and configured to visually display at least one indication, a touch sensitive area located on the substrate and electrically connectable to the electronic display, and a processor connected to the electronic display and configured to modify the visual appearance of the at least one indication in response to a user touching or depressing the touch sensitive area.

20 Claims, 5 Drawing Sheets

(52) U.S. Cl.
CPC ............ *A61M 2005/31588* (2013.01); *A61M 2205/3553* (2013.01); *A61M 2205/505* (2013.01); *A61M 2205/52* (2013.01)

(56) References Cited

U.S. PATENT DOCUMENTS

| | | |
|---|---|---|
| 2009/0069745 A1 | 3/2009 | Estes et al. |
| 2015/0343152 A1 | 12/2015 | Butler et al. |
| 2016/0263327 A1 | 9/2016 | Radmer et al. |
| 2018/0093042 A1 | 4/2018 | Klemm et al. |

FOREIGN PATENT DOCUMENTS

| | | | |
|---|---|---|---|
| CN | 105263547 | 1/2016 | |
| CN | 206526352 | 9/2017 | |
| JP | 2016-512966 A | 5/2016 | |
| WO | WO 2004/078239 | 9/2004 | |
| WO | WO 2004/078240 | 9/2004 | |
| WO | WO 2004/078241 | 9/2004 | |
| WO | WO 2009/136209 | 11/2009 | |
| WO | WO 2013/120777 | 8/2013 | |
| WO | WO 2014/166915 | 10/2014 | |
| WO | WO 2014/209634 | 12/2014 | |
| WO | WO 2016/055620 | 4/2016 | |
| WO | WO 2017/081051 | 5/2017 | |
| WO | WO-2017081051 A1 * | 5/2017 | ........ A61M 5/31553 |
| WO | WO 2018/036938 | 3/2018 | |

OTHER PUBLICATIONS

International Preliminary Report on Patentability in Appln. No. PCT/EP2019/062579, dated Nov. 17, 2020, 6 pages.

PCT International Search Report and Written Opinion in International Appln. No. PCT/EP2019/062579, dated Jul. 10, 2019, 8 pages.

* cited by examiner

TOUCH SENSITIVE LABEL FOR AN INJECTION DEVICE

CROSS REFERENCE TO RELATED APPLICATIONS

The present application is the national stage entry of International Patent Application No. PCT/EP2019/062579, filed on May 16, 2019, and claims priority to Application No. EP 18305608.4, filed on May 17, 2018, the disclosures of which are incorporated herein by reference.

TECHNICAL FIELD

The present disclosure relates to the field of labels for injection devices. In particular, the present disclosure relates to a touch sensitive label for an injection device that is configured to change its visual appearance in response to a user touching a touch sensitive area of the label. In another aspect the disclosure relates to a reminder device attachable to an injection device and configured to remind and/or to assist a user to conduct an injection procedure when making use of the injection device.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such as diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod to operably engage with a bung or piston of the cartridge. By means of the drive mechanism and its piston rod, the bung or piston of the cartridge is displaceable in a distal or dispensing direction and may therefore expel a predefined amount of the medicament via a piercing assembly, e.g. in form of an injection needle, which is to be releasably coupled with a distal end section of the housing of the drug delivery device.

The medicament to be dispensed by the drug delivery device may be provided and contained in a multi-dose cartridge. Such cartridges typically comprise a vitreous barrel sealed in distal direction by means of a pierceable seal and being further sealed in proximal direction by the bung. With reusable drug delivery devices an empty cartridge is replaceable by a new one. In contrast to that, drug delivery devices of disposable type are to be entirely discarded when the medicament in the cartridge has been dispensed or used-up.

With some drug delivery devices, such as pen-type injection devices a user has to set a dose of equal or variable size by rotating a dose dial in a clockwise or dose-incrementing direction relative to a body or housing of the injection device. For injecting and expelling of a dose of a liquid medicament the user has to depress a trigger or dose button in a distal direction and hence towards the body or housing of the injection device. Typically, the user uses his thumb for exerting a distally directed pressure onto the dose button, which may be located at a proximal end of the dose dial and the dose dial sleeve, while holding the housing of the injection device with the remaining fingers of the same hand.

For mechanically implemented injection devices it is desirable to enable a precise, reliable and quasi-automated supervision and/or collection of injection-related data during use of the injection device. Moreover there is a rising demand of user assistance for the proper and regular handling of such drug delivery or injection devices. For a successful therapy a well-defined, e.g. user specific amount of a medicament, i.e. a dose of the medicament, must be administered in accordance to a given prescription schedule, e.g. on a regular temporal basis. In some instances a patient may have forgotten or may not be aware if a prescribed dose was recently injected or not. Moreover, the patient may not always be aware about the size of the dose to be set and injected. This is of particular relevance for patients being oblivious and/or for patients being mentally and/or physically infirm at least to a certain degree.

Summary

The present disclosure provides a solution to the above described drawbacks regarding a proper handling of an injection device. It is also provides a memory aid and/or a reminder for a user for an accurate operation of the injection device. The reminder or memory aid should be easy and intuitive to use. It should be manufacturable at moderate or low costs and should enable retrofitting existing injection devices with a memory aid or with a reminder. The memory aid or reminder should further provide a space saving design and should conform to the geometry of a housing of an injection device.

In one aspect the disclosure relates to a touch sensitive label for an injection device. The label comprises a flexible substrate configured for attachment to a housing of the injection device. The touch sensitive label comprises an electronic display located on the substrate. The electronic display is configured to visually display at least one indication. The touch sensitive label further comprises a touch sensitive area that is located on the substrate. The touch sensitive area is electrically connectable to the electronic display. The touch sensitive area may be electrically connected to the electronic display. It may be permanently electrically connected to the electronic display. It may be also electrically disconnected from the electronic display. The touch sensitive label further comprises a processor electrically connected to the display. The processor is operable to control and to modify the display. The processor is configured to modify the visual appearance of the at least one indication in response to a user touching or depressing the touch sensitive area.

The flexible substrate may be one of the elastically and plastically deformable. In particular, the flexible substrate may be configured to plastically deform and to conform to an outer shape and size or geometry of a housing of an injection device.

In this way the touch sensitive label is configured to mark and to characterize a housing of an injection device, namely when the touch sensitive label is attached to the housing of the injection device and when the electronic display visually displays the at least one indication. The at least one indication represents a visual identifier for the injection device. The at least one indication may represent a size of a dose to be set or a point of time at which a dose should be set and injected by the user with the aid of the injection device. In this way the touch sensitive label provides an interactive a memory aid and/or reminder for persons or patients using the injection device equipped with the touch sensitive label.

The electronic display may be switchable between a default mode and an activated mode. The activated mode may be also denoted as a prompted mode. In the default mode the electronic display and the processor may be configured to permanently display the at least one indication. The at least one indication may be visible on the display as long as the touch sensitive area is not touched or tipped, e.g. by a finger of the user. In response to a user touching or depressing the touch sensitive area the processor is configured to modify the visual appearance of the electronic display. Generally, the processor and the display may react in accordance to a variety of modes. Upon touching or depressing the touch sensitive area the electronic display may be switched from the default mode into the activated mode; or vice versa.

For both, the default mode and the activated mode there are different scenarios. According to one scenario the electronic display is configured to visualize the at least one indication as long as in the default mode. In the activated mode and upon touching or depressing the touch sensitive area the at least one indication disappears at least for a predefined time interval. In the activated mode the electronic display may represent a blank screen and may be void of any visual indications. When a user repeatedly touches or depresses the touch sensitive area the electronic display may switch back from the activated mode into the default mode. Consequently, the at least one indication may reappear on the electronic display.

Alternative, the processor and the electronic display may be configured to provide a first visual indication when in the default mode. When switched into the activated mode the electronic display may provide or comprise a second visual indication that distinguishes from the first visual indication.

The electronic display and its interaction with the touch sensitive area may be configured such that the depressing or touching of the touch sensitive area switches the electronic display into the activated mode when in the default mode. In a different situation, wherein the electronic display is in the activated mode touching or depressing of the touch sensitive area switches the electronic display from the activated mode into the default mode. The electronic display may be configured to remain in one of the default mode and the activated mode as long as the touch sensitive area is not touched or depressed. Switching between the default mode and the activated mode may always require touching or depressing of the touch sensitive area.

In this way a user is given the possibility to selectively switch on and switch off the at least one indication on demand. In a situation, in which the user or patient may have forgotten the size of the dose to be set and to be dispensed he may simply look to the touch sensitive label and read the at least one indication provided on the electronic display. If the at least one indication should not be visible on the electronic display the user may simply touch or depress the touch sensitive area thus triggering a visual appearance of the at least one indication informing the user about the prescribed dose of the medicament that is currently due for injection.

With another example the electronic display may be configured to switch into the default mode after a predefined time interval has lapsed since the touch sensitive area has been touched or depressed. With such a configuration the electronic display may permanently visualize the at least one indication. Upon and in response to a user touching or depressing the touch sensitive area the electronic display switches into the activated mode for a predefined time interval. After the time interval has lapsed the electronic display may be configured to return into the default mode without any user interaction. In the activated mode the electronic display may be void of the at least one indication and may provide only a blank screen thus indicating to a user, that setting and injecting of a dose is currently not due.

With another example the electronic display may be configured to switch into the activated mode after a predefined time interval has lapsed since the touch sensitive area has been touched or depressed. Here, in the activated mode, the display may be void of a visual indication. It may represent or provide a blank screen. This might be of benefit for saving electrical energy when the electronic display is implemented as an active display, i.e. comprising an active illumination.

For a typical scenario of use the user should touch or depress the electronic display after or immediately before a dose setting and injection procedure has been conducted. As a consequence, the at least one indication will disappear on the electronic display thus indicating to a user, that the next injection is not currently due. In this way and each time the user looks at the touch sensitive label he can easily be certain whether an injection procedure that was due quite a while ago was actually conducted or not.

Instead of disappearing of the at least one indication it is also conceivable that in the activated mode the electronic display provides a second indication thus indicating to a user when a subsequent injection procedure is due or when a last injection procedure was actually executed.

Hence, the electronic display may be configured to visualize not only the at least one indication but it may also be configured to visualize a confirmation and/or an indication for the user regarding a previous or a preceding injection procedure.

The flexible substrate is particularly configured to wrap around at least a portion of the housing of the injection device. The housing may comprise a somewhat cylindrical or tubular structure. The flexible substrate may hence conform or customize to a sidewall of the tubular shaped housing of the injection device. The flexible substrate enables a rather universal attachment of the touch sensitive label to a multitude of different injection devices. The touch sensitive label may be universally applicable and/or attachable to different types of injection devices.

The touch sensitive label is also rather thin or flat and can be permanently attached to the housing of the injection device. The injection device with the touch sensitive label attached thereto can be wrapped or packed in a device packaging, e.g. for transportation and/or storage. If at all, the touch sensitive label only has a minor impact on the outer contour and/or geometry of the injection device when attached to the housing of the injection device. The touch sensitive label may further impart a rather attractive design to the injection device.

The flexible substrate may comprise a flexible plastic foil or a flexible metal foil. The flexible substrate may comprise a plastic foil e.g. made of polyethylene (PE) or polyethylene terephthalate (PET).

The flexible substrate, the electronic display, the touch sensitive area and hence the entire touch sensitive label may comprise a total thickness of less than 5 mm, less than 4 mm, less than 3 mm or less than 2 mm. With some examples the touch sensitive label comprises a thickness of less than 1 mm or less than 0.5 mm.

With some examples the touch sensitive area comprises at least one capacitive switch. It may comprise numerous capacitive switches spatially distributed across the touch sensitive area. The at least one capacitive switch can be produced in printing electronics technology. For instance, a portion of the touch sensitive area may comprise an electrode which is part of a capacitor. The capacitor can be "detuned" when an object, such as a finger of a user approaches and comes in close vicinity or in mechanical contact to the capacitor. This approach has an influence on a measurable property of the capacitor, e.g. on the capacitance thereof. According to a further example the label comprises an electronic circuit located on the substrate. The electronic circuit is electrically connected to the touch sensitive area and the electronic circuit is further electrically connected to the electronic display and to the processor. With numerous examples of the label, wherein the touch sensitive area is located offset or remote from the electronic display the electronic display and the touch sensitive area are electrically connected or connectable by the electronic circuit. The electronic circuit may be directly arranged on the flexible substrate. The touch sensitive area, the electronic display and/or the processor may be integrated into the electronic circuit.

The electronic circuit may comprise a flexible electronic circuit. Hence, electrically conductive structures of the electronic circuit are bendable or pliable so as to follow a flexible deformation of the substrate, e.g. in the course of attaching the flexible substrate to the housing of the injection device, e.g. through wrapping the label to the tubular shaped housing.

The electronic circuit may be printed on the substrate. The electronic circuit may be printed on the flexible substrate by one or more inks that are composed of carbon-based compounds. Moreover, the electronic circuit may be deposited on the flexible substrate by a solution-based or vapor-based deposition process. A printed electronic circuit on the substrate enables a low cost volume fabrication of the touch sensitive label.

According to another example the touch sensitive area is integrated into the electronic display. In other words, the electronic display comprises a touch sensitive electronic display. The touch sensitive area may overlap with the display surface. The touch sensitive area may also overlap with the at least one indication visually displayed on the electronic display. In this way, a rather intuitive look and feel can be provided. The user may simply touch the at least one indication in order to invoke a switching of the touch sensitive label from the default mode into the activated mode or vice versa.

In another example a lower side of the flexible substrate is at least in sections provided with an adhesive. The lower side of the flexible substrate may be provided with an adhesive layer. The entire lower side of the flexible substrate or only portions thereof may be provided with the adhesive. Especially the border regions of the lower side of the flexible substrate are provided with the adhesive in order to enable a permanent attachment of the label to the housing of the injection device. By means of the adhesive on the lower side of the flexible substrate an adhesion-based fixing of the touch sensitive label to the housing of the injection device can be provided. This is rather space saving and can be implemented at moderate or low cost.

When handed out to customers or to patients the lower side of the flexible substrate and hence the adhesive provided thereon may be covered by a release sheet protecting the adhesive as long as the touch sensitive label is not in use. Prior to an attachment of the touch sensitive label to the housing of the injection device the release sheet has to be removed thus exposing the adhesive at the lower side of the flexible substrate.

The adhesive at the lower side of the flexible substrate provides an adhesive effect or force in the interface between the label and a housing of an injection device. This adhesive force is larger than an optional inherent elastic restoring force of the label or substrate when or after it has been subject to an elastic and/or plastic deformation to conform to the outer shape of the housing of the injection device.

According to another example the electronic circuit further comprises a battery. The battery is typically connected to the processor and/or to the electronic display. The processor and/or the battery may be printed on the flexible substrate. The processor and/or the battery may also be flexible to a certain degree thus allowing and supporting a deformation of the flexible substrate upon assembly and attachment to the housing of the injection device.

The processor is connected to the electronic display and is also connected to the battery. The processor is driven by electric energy provided by the battery. Typically, both the processor and the battery comprise or are made of printed electronic components. Moreover, the processor may also be connected to the touch sensitive area. The processor may be configured to process electronic signals provided or generated by the touch sensitive area in order to switch the electronic display from the default mode into the activated mode and/or vice versa from the activated mode into the default mode.

The processor may further be configured to modify the at least one indication on the electronic display. The processor may be deployed to visualize only one and the same indication on the electronic display. The processor and/or the electronic display may be reconfigurable to visualize different indications on the electronic display. In a typical scenario the injection device should be used to repeatedly and regularly set and dispense only one or a limited number of different doses of the medicament. Accordingly, the processor and the electronic display may be configured to display always one and the same indication. The processor may be of programmable type. It may be reprogrammed or reconfigured to modify the at least one indication to become visually displayed on the electronic display.

According to another example the electronic circuit comprises a data storage or memory configured to store at least one of a number of user activities and a point of time of a user activity or of numerous user activities. The electronic circuit and/or the processor may be further equipped with a clock to derive a time indication and in order to enable storage of a point of time of a user activity, e.g. a point of time at which a user touches or depresses the touch sensitive area. If the label is void of a clock the electronic circuit may be simply configured to count a number of such user activities. In this way, a kind of a dosage counter can be provided by the touch sensitive label.

According to another example the electronic circuit comprises an antenna for wireless transmission of electronic signals with an external electronic device. The antenna is typically connected to the processor. By means of the antenna the processor is configured to communicate with an external electronic device. The processor may be configured to transmit data to the external electronic device. The processor may be configured to receive data from the external electronic device. The external electronic device may comprise a handheld external electronic device, such as a smartphone, a smart watch or a tablet computer. The antenna may be further enabled to provide communication with a personal computer or similar computing devices.

The antenna and its interaction with the processor further enables a transfer of data previously stored in the data storage of the electronic circuit to the external electronic device. By means of the antenna the external electronic device may be configured to read out the content of the data storage of the touch sensitive label. Typically, the data storage is integrated into the electronic circuit. With other examples it may be provided separately, hence offset from the electronic circuit. The wireless transmission of electronic signals between the processor and the external electronic device further enables a reconfiguring of the processor and/or of the electronic display.

By means of the external electronic device and the wireless transmission of electronic signals the external electronic device may be used to reconfigure the touch sensitive label. In this way, the at least one indication may be replaced by a second indication. In addition, the total appearance of the electronic display may be reconfigured in accordance to electronic signals received from the external electronic device. In this way, the touch sensitive label can be individually configured for different usage scenarios.

The transmission of data stored in the data storage of the electronic circuit to the external electronic device enables a monitoring and post-dispensing evaluation of user activities that were recorded in the data storage at during time intervals during which the touch sensitive label is disconnected from the external electronic device.

According to another example the electronic circuit comprises a sensor configured to determine at least a position and or rotational state of at least one of a dose tracker and a preselector of the injection device when the label is attached to the injection device. The dose tracker, in particular its position or rotational state relative to the housing of the injection device is unequivocally indicative of a size of a dose actually set or dispensed. The sensor implemented in the touch sensitive label is configured to determine a position or a rotational state of the dose tracker relative to the housing of the injection device when the label is correctly attached to a predefined location of the housing of the injection device.

An optional preselector of the injection device may be configured to determine a maximum size of a dose to be set by the device. Insofar the preselector limit the number and social the size of doses to be set and dispensed by the injection device.

The preselector may be displaceable relative to the housing along the longitudinal axis. The preselector may be lockable to the housing, in particular to the sidewall thereof in at least two different positional states relative to the housing. Here, the positional state may refer to a longitudinal position of the preselector relative to the housing. The positional state may also refer to an angular orientation of the preselector relative to the housing when the preselector is rotatably supported in or relative to the housing.

Typically, the preselector is displaceable at least between a first preselection positional state and a second preselection positional state. The first preselection positional state may coincide with a distal stop position of preselector relative to the housing. The second preselection positional state may coincide with a proximal stop position of the preselector relative to the housing. In the second preselection positional state the preselector may be located closer to a proximal end of the housing in the first preselection positional state. In any of the at least two preselection positional states the preselector is lockable to the housing.

A specific portion of the sidewall of the housing, to which the preselector is lockable may define a positional state at which a longitudinal or rotational displacement of the dose tracker is blocked. Hence, the dose tracker is hindered by the preselector from moving beyond the positional or rotational state defined by the position of the preselector relative to the sidewall of the housing.

In other words, when the dose tracker reaches a maximum dose positional state it may abut or engage with the preselector which is least temporally locked to a predefined portion or section of the sidewall. The preselector may comprise a preselector stop feature and the dose tracker may comprise a tracking stop feature. The preselector stop feature and the tracking stop feature may comprise mutually corresponding stop faces, e.g. extending in circumferential and/or radial direction so as to engage axially. Alternatively or additionally, the preselector stop feature and the tracking stop feature comprise mutually corresponding stop faces extending in axial direction and radial direction so as to engage circumferentially. When configured to engage axially, the mutual engagement of the preselector stop feature and the tracking stop feature provides an axial stop thereby impeding and blocking a longitudinal or axial translation of the dose tracker beyond a predefined maximum axial dose positional state.

With the sensor the touch sensitive label may not only provide information to a user but may also collect information about the actual handling and performance of the injection device. In this way, the processor of the touch sensitive label is enabled and configured to compare a predefined or prescribed dose size stored in the data storage of the electronic circuit with a dose size actually determined on the basis of signals obtained from the sensor during use of the injection device. Alternative or in addition the sensor may enable visualization of a momentary positional state of the preselector.

In this way, the processor of the touch sensitive label is configured to determine if a prescribed dose has been correctly set and injected by a user. The processor and hence the touch sensitive label may thus supervise and/or monitor the proper operation of the injection device in view of a given therapy or prescription schedule.

With another example the sensor comprises at least a first sensor segment and a second sensor segment arranged at a predefined distance from each other. Each one of the first and second sensor segments is configured to detect a presence or position of an indicator of at least one of the dose tracker and the preselector. The indicator is particularly configured for position sensing through the sensor. The indicator may be encoded in accordance to the sensitivity of the sensor. If the sensor is implemented as an electrical sensor, such as a resistive sensor, the indicator of the dose tracker comprises a characteristic electrical resistance.

As the indicator of the dose tracker and/or preselector gets in direct electric connection with one of the sensor segments the resistivity of the respective sensor segment will change accordingly, which change in resistivity is detectable by the sensor and/or by the processor connected thereto.

With other implementations the sensor and the indicator are configured as a magnetic position or rotation sensor. Hence, the sensor segments may comprise Hall sensor or coiled segments. The indicator may comprise a particular magnetic encoding detectable by the sensor segments of the sensor. A magnetic encoding combined with a magnetic and/or electromagnetic detection enables a touchless sensing of a position or rotational state of the dose tracker of the injection device. The sensor and the corresponding indicator may also be implemented on the basis of an electric capacity measurement.

With other examples the sensor may comprise only one or a few sensor segments while the dose tracker is provided with numerous indicators adjacently arranged along the movement direction of the dose tracker. Indicators adjacently arranged on the dose tracker may distinguish from each other with regard to at least one property detectable by the sensor. Numerous indicators on the dose tracker or preselector may provide one of an electrical, magnetic or capacitive encoding. As the dose tracker or preselector is subject to a movement relative to the housing of the injection device and hence relative to the at least one sensor segment of the sensor the numerous indicators induce mutually distinguishing sensor signals as they pass by the sensor or sensor segments. Here, the sensor or sensor segment is configured to generate an varying electrical signal as different indicators pass along the sensor.

According to another example the processor is configured to determine at least one of the longitudinal or rotational position of the dose tracker or preselector relative to the housing on the basis of an electronic signal obtained from the sensor. In this way, the processor is configured to determine the position or rotational state of the dose tracker which is indicative of the size of a dose actually set with the injection device. The processor is thus configured to determine a size of a dose actually set with the injection device when the touch sensitive label is appropriately attached to the housing of the injection device. Likewise, the processor is configured to determine a positional state of a preselector and hence a maximum size of a dose that can be set and injected with the injection device.

In another example the processor is also configured to compare the at least one of the determined longitudinal or rotational position of the dose tracker with a predefined position. The predefined position may correspond to a prescribed size of a dose. Since the processor is able to compare an actually determined positional or rotational state of the dose tracker with the predefined position the processor is hence enabled to compare a dose size actually determined or measured with a prescribed or predefined dose size. In this way the touch sensitive label is enabled to monitor and to keep track if a user sets a dose of a correct size or if a dose set by the user does not match with a predefined dose size.

The sensor and/or the processor may be further configured to determine both, a positional state of the dose tracker and a positional state of the preselector. Then, the processor may be configured to compare the positional state of the dose tracker with the positional state of the preselector and hence to compare a dose actually set with a maximum dose settable and injectable with the injection device. In this way, the processor may be configured to determine if a maximum or predefined size of a dose as governed by the positional state of the preselector has been set and subsequently dispensed.

According to a further example the processor is configured to generate at least one of a visual indication and a visual confirmation on the electronic display. The processor might be configured to generate a visual confirmation in response to a user touching or depressing the touch sensitive area. In this way the user is provided with a feedback that the touching or depression of the touch sensitive area has been registered and detected by the touch sensitive label.

According to a further example the processor is configured to generate at least one of a visual indication and a visual confirmation on the electronic display if the determined longitudinal or rotational position of the dose tracker matches with the predefined position or if the determined longitudinal or rotational position of the dose tracker does not match with the predefined position. A visual confirmation may only be presented on the electronic display if the determined longitudinal or rotational position of the dose tracker matches with the predefined position. As long as the determined longitudinal or rotational position of the dose tracker does not match with the predefined position, typically corresponding to a predefined or prescribed size of a dose, the processor and the electronic display may be configured to generate a visual indication thus informing the user that the dose actually set does not match the predefined or prescribed size of the dose. Hence, the dose actually set may be too small or too large.

The visual indication may be provided on the electronic display in form of a symbol, e.g. in form of an arrow thus indicating to a user that the dose actually set is too small or too large. The visual indication may be directly indicative about a sense of rotation or may be indicative about a direction the dose tracker and/or a dose setting member, e.g. represented by a dose dial, has to be moved or rotated in order to minimize a difference between a dose actually set and a predefined or prescribed size of a dose.

With some examples the processor is configured to permanently generate or provide the at least one visual indication thus informing the user about the predefined or prescribed size of a dose and/or informing the user with regard to a direction a dose setting member, e.g. a dose dial has to be moved to arrive at the predefined or prescribed dose. Upon determining that the longitudinal or rotational position of the dose tracker matches with the predefined position the processor may be configured to visually illustrate the visual confirmation at the expense of the visual indication. Here, the visual indication may disappear as the visual confirmation appears on the electronic display. With another example, the visual confirmation may be provided in addition to the visual indication as soon the determined longitudinal or rotational position of the dose tracker matches with the predefined position.

With a further example, the visual confirmation may be provided in form of a modification of the visual appearance of the visual indication. Hence, upon determination that the longitudinal rotational position of the dose tracker matches with the predefined dose the visual indication may change. Here, an arrow may be replaced by a confirmation symbol, such as a checkmark or tickmark. With other examples, a color, a brightness or a style of the visual indication may change. E.g., a number, letter of symbol may be framed or may be represented in italics or bold face. Thus, the processor may be configured to change the visual indication upon determination that the longitudinal or rotational position of the dose tracker matches with the predefined position.

The optional preselector may be configured to modify the predefined position stored in the data storage of the processor. The preselector is typically configured to mechanically interact with the dose tracker in order to define a maximum dosing position of the dose tracker. In this way, the positional state of the preselector relative to the housing is indicative of a maximum or predefined size of a dose to be set and dispensed by the injection device. By determining the positional state of the preselector through the sensor, the predefined size of a dose to be set and dispensed can be automatically detected by the sensor and can be stored in the data storage of the processor. Depending on the positional state of the preselector the predefined dose size stored in the storage of the touch sensitive label can be changed.

In this way the label may visually assist a user during setting of a correct and prescribed dose of the medicament.

According to another example the electronic circuit comprises at least one printed electronic component. In other examples the electronic circuit consists of printed electronic components. The entire electronic circuit may comprise or may consist of printed electronic components. Typically, the electronic circuit is printed on an upper side of the flexible substrate. The printed electronic components of the electronic circuit as well as printed conductive structures of the electronic circuit are flexible to a predefined degree thus allowing a flexible deformation and bending of the electronic circuit, e.g. in the course of wrapping the touch sensitive label around the housing of the injection device.

According to another example the electronic display is one of an electrophoretic display and a thin film electroluminescent display. Such display types consume only a minimum of electrical energy. In this way, a battery printed on the flexible substrate may provide sufficient electric energy to enable a failure safe operation of the touch sensitive label and its electronic display for a time that exceeds the lifetime of the injection device and/or of the medicament located therein.

Electrophoretic displays and thin film electroluminescent displays further provide a rather large contrast and are easily legible also in direct sunlight. They consume only a minimum of electric power, in particular when switching from one display state to another display state.

According to another aspect the disclosure also relates to an injection device for setting and injecting of a dose of a medicament. The injection device may be configured as a handheld pen-type injector or as a medicament pump. The injection device comprises a housing configured to accommodate a medicament container. The injection device further comprises a drive mechanism configured to withdraw or to expel a dose of the medicament from the medicament container. The drive mechanism is further configured to inject the dose of the medicament into biological tissue. The injection device is further provided with a label as described above. The label is attached to the housing of the injection device.

The drive mechanism of the injection device typically comprises a piston rod displaceable along a longitudinal direction. The piston rod is configured to operably engage with a piston of a cartridge containing the injectable medicament. A distal end of the cartridge located opposite to the piston rod is provided with a pierceable seal that is typically penetrable by a double tipped injection needle.

With the touch sensitive label attached to the outside of the housing of the injection device an all mechanically implemented injection device, such as a disposable or reusable injection pen can be retrofitted with a memory aid or reminder thus assisting a user with regards to a proper handling and operation of the injection device.

According to a further example the medicament container, e.g. in form of a cartridge containing the medicament is arranged inside the housing of the injection device. The injection device may be configured as a disposable injection device. The medicament container filled with the medicament may be readily assembled inside the injection device as the injection device is handed out to customers or patients.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE FIGURES

In the following, numerous examples of the container and of an injection device will be described in greater detail by making reference to the following drawings.

DETAILED DESCRIPTION

Figure 1:
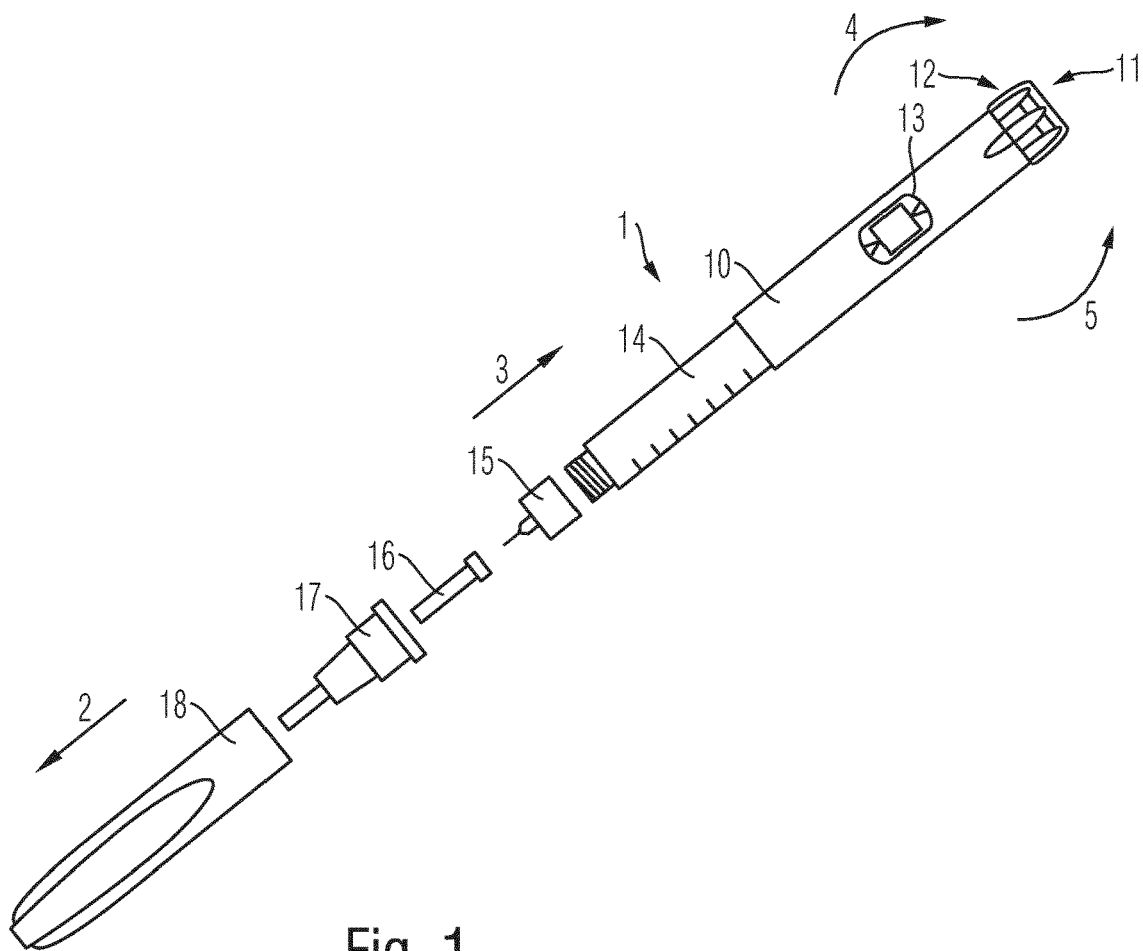
FIG. 1 shows an example of an injection device.
Figure 2:
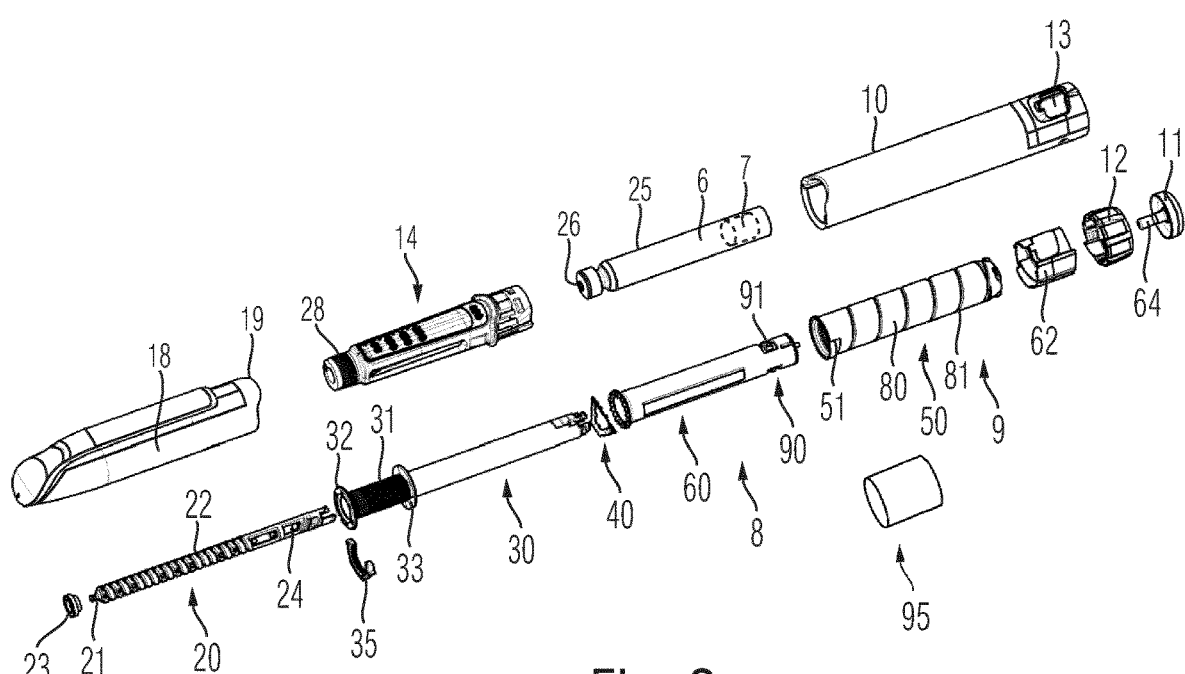
FIG. 2 shows the injection device of FIG. 1 in an exploded perspective view.

The injection device 1 as shown in FIGS. 1 and 2 is a pre-filled disposable injection device that comprises a housing 10 to which an injection needle 15 can be affixed. The injection needle 15 is protected by an inner needle cap 16 and either an outer needle cap 17 or a protective cap 18 that is configured to enclose and to protect a distal section of the housing 10 of the injection device 1. The housing 10 may comprise and form a main housing part configured to accommodate a drive mechanism 8 as shown in FIG. 2. The injection device 1 may further comprise a distal housing component denoted as cartridge holder 14. The cartridge holder 14 may be permanently or releasably connected to the main housing 10. The cartridge holder 14 is typically configured to accommodate a cartridge 6 that is filled with a liquid medicament. The cartridge 6 comprises a cylindrically-shaped or tubular-shaped barrel 25 sealed in proximal direction 3 by means of a bung 7 located inside the barrel 25. The bung 7 is displaceable relative to the barrel 25 of the cartridge 6 in a distal direction 2 by means of a piston rod 20. A distal end of the cartridge 6 is sealed by a pierceable seal 26 configured as a septum and being pierceable by a proximally directed tipped end of the injection needle 15. The cartridge holder 14 comprises a threaded socket 28 at its distal end to threadedly engage with a correspondingly threaded portion of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dose dial 12 at a proximal end of the injection device 1 may be displayed in so-called international units (IU, wherein 1 IU is the biological equivalent of about 45.5 µg of pure crystalline insulin (1/22 mg). The dose dial 12 may comprise or may form a dose dial.

As shown further in FIGS. 1 and 2, the housing 10 comprises a dosage window 13 that may be in the form of an aperture in the housing 10. The dosage window 13 permits a user to view a limited portion of a number sleeve 80 that is configured to move when the dose dial 12 is turned, to provide a visual indication of a currently set dose. The dose dial 12 is rotated on a helical path with respect to the housing 10 when turned during setting and/or dispensing or expelling of a dose.

The injection device 1 may be configured so that turning the dosage knob 12 causes a mechanical click sound to provide acoustical feedback to a user. The number sleeve 80 mechanically interacts with a piston in the insulin cartridge 6. When the needle 15 is stuck into a skin portion of a patient, and when the trigger 11 or injection button is pushed, the insulin dose displayed in display window 13 will be ejected from injection device 1. When the needle 15 of the injection device 1 remains for a certain time in the skin portion after the trigger 11 is pushed, a high percentage of the dose is actually injected into the patient's body. Ejection of an insulin dose may also cause a mechanical click sound, which is however different from the sounds produced when using the dose dial 12.

In this embodiment, during delivery of the insulin dose, the dose dial 12 is turned to its initial position in an axial movement, that is to say without rotation, while the number sleeve 80 is rotated to return to its initial position, e.g. to display a dose of zero units.

The injection device 1 may be used for several injection processes until either the cartridge 6 is empty or the expiration date of the medicament in the injection device 1 (e.g. 28 days after the first use) is reached.

Furthermore, before using injection device 1 for the first time, it may be necessary to perform a so-called "prime shot" to remove air from the cartridge 6 and the needle 15, for instance by selecting two units of the medicament and pressing trigger 11 while holding the injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user.

An example of the drive mechanism 8 is illustrated in more detail in FIG. 2. It comprises numerous mechanically interacting components. A flange like support of the housing 10 comprises a threaded axial through opening threadedly engaged with a first thread or distal thread 22 of the piston rod 20. The distal end of the piston rod 20 comprises a bearing 21 on which a pressure foot 23 is free to rotate with the longitudinal axis of the piston rod 20 as an axis of rotation. The pressure foot 23 is configured to axially abut against a proximally facing thrust receiving face of the bung 7 of the cartridge 6. During a dispensing action the piston rod rotates relative to the housing 10 thereby experiencing a distally directed advancing motion relative to the housing 10 and hence relative to the barrel 25 of the cartridge 6. As a consequence, the bung 7 of the cartridge 6 is displaced in distal direction 2 by a well-defined distance due to the threaded engagement of the piston rod 20 with the housing 10.

The piston rod 20 is further provided with a second thread 24 at its proximal end. The distal thread 22 and the proximal thread 24 are oppositely handed.

There is further provided a drive sleeve 30 having a hollow interior to receive the piston rod 20. The drive sleeve 30 comprises an inner thread threadedly engaged with the proximal thread 24 of the piston rod 20. Moreover, the drive sleeve 30 comprises an outer threaded section 31 at its distal end. The threaded section 31 is axially confined between a distal flange portion 32 and another flange portion 33 located at a predefined axial distance from the distal flange portion 32. Between the two flange portions 32, 33 there is provided a last dose limiter 35 in form of a semi-circular nut having an internal thread mating the threaded section 31 of the drive sleeve 30.

The last dose limiter 35 further comprises a radial recess or protrusion at its outer circumference to engage with a complementary-shaped recess or protrusion at an inside of the sidewall of the housing 10. In this way the last dose limiter 35 is splined to the housing 10. A rotation of the drive sleeve 30 in a dose incrementing direction 4 or clockwise direction during consecutive dose setting procedures leads to an accumulative axial displacement of the last dose limiter 35 relative to the drive sleeve 30. There is further provided an annular spring 40 that is in axial abutment with a proximally facing surface of the flange portion 33. Moreover, there is provided a tubular-shaped clutch 60. At a first end the clutch 60 is provided with a series of circumferentially directed saw teeth. Towards a second opposite end of the clutch 60 there is located a radially inwardly directed flange.

Furthermore, there is provided a dose dial sleeve also denoted as number sleeve 80. The number sleeve 80 is provided outside of the spring 40 and the clutch 60 and is located radially inward of the housing 10. A helical groove 81 is provided about an outer surface of the number sleeve 80. The housing 10 is provided with the dosage window 13 through which a part of the outer surface of the number 80 can be seen. The housing 10 is further provided with a helical rib at an inside sidewall portion of an insert piece 62, which helical rib is to be seated in the helical groove 81 of the number sleeve 80. The tubular shaped insert piece 62 is inserted into the proximal end of the housing 10. It is rotationally and axially fixed to the housing 10. There are provided first and second stops on the housing 10 to limit a dose setting procedure during which the number sleeve 80 is rotated in a helical motion relative to the housing 10. As will be explained below in greater detail, at least one of the stops is provided by a preselector stop feature 71 provided on a preselector 70.

The dose dial 12 in form of a dose dial grip is disposed about an outer surface of the proximal end of the number sleeve 80. An outer diameter of the dose dial 12 typically corresponds to and matches with the outer diameter of the housing 10. The dose dial 12 is secured to the number 80 to prevent relative movement there between. The dose dial 12 is provided with a central opening.

The trigger 11, also denoted as dose button is substantially T-shaped. It is provided at a proximal end of the injection device 10. A stem 64 of the trigger 11 extends through the opening in the dose dial 12, through an inner diameter of extensions of the drive sleeve 30 and into a receiving recess at the proximal end of the piston rod 20. The stem 64 is retained for limited axial movement in the drive sleeve 30 and against rotation with respect thereto. A head of the trigger 11 is generally circular. The trigger side wall or skirt extends from a periphery of the head and is further adapted to be seated in a proximally accessible annular recess of the dose dial 12.

To dial a dose a user rotates the dose dial 12. With the spring 40 also acting as a clicker and the clutch 60 engaged, the drive sleeve 30, the spring or clicker 40, the clutch 60 and the number sleeve 80 rotate with the dose dial 12. Audible and tactile feedback of the dose being dialed is provided by the spring 40 and by the clutch 60. Torque is transmitted through saw teeth between the spring 40 and the clutch 60. The helical groove 81 on the number sleeve 80 and a helical groove in the drive sleeve 30 have the same lead. This allows the number sleeve 80 to extend from the housing 10 and the drive sleeve 30 to climb the piston rod 20 at the same rate. At a limit of travel a radial stop on the number sleeve 80 engages either with a first stop or a second stop provided on the housing 10 to prevent further movement in a first sense of rotation, e.g. in a dose incrementing direction 4. Rotation of the piston rod 20 is prevented due to the opposing directions of the overall and driven threads on the piston rod 20.

The last dose limiter 35 keyed to the housing 10 is advanced along the threaded section 31 by the rotation of the drive sleeve 30. When a final dose dispensed position is reached, a radial stop formed on a surface of the last dose limiter 35 abuts a radial stop on the flange portion 33 of the drive sleeve 30, preventing both, the last dose limiter 35 and the drive sleeve 30 from rotating further.

Should a user inadvertently dial beyond the desired dosage, the injection device 1, configured as a pen-injector allows the dosage to be dialed down without dispense of the medicament from the cartridge 6. For this the dose dial 12 is simply counter-rotated. This causes the system to act in reverse. A flexible arm of the spring or clicker 40 then acts as a ratchet preventing the spring 40 from rotating. The torque transmitted through the clutch 60 causes the saw teeth to ride over one another to create the clicks corresponding to dialed dose reduction. Typically, the saw teeth are so disposed that a circumferential extent of each saw tooth corresponds to a unit dose. Here, the clutch may serve as a ratchet mechanism.

As an alternative or in addition the ratchet mechanism 90 may comprise at least one ratchet feature 91, such as a flexible arm on the sidewall of the tubular-shaped clutch 60. The at least one ratchet feature 91 may comprise a radially outwardly extending protrusion e.g. on a free end of the flexible arm. The protrusion is configured to engage with a correspondingly shaped counter ratchet structure on an inside of the number sleeve 80. The inside of the number sleeve 80 may comprise longitudinally shaped grooves or protrusions featuring a saw-tooth profile. During dialing or setting of a dose the ratchet mechanism 90 allows and supports a rotation of the number sleeve 80 relative to the clutch 60 along a second sense of rotation 5, which rotation is accompanied by a regular clicking of the flexible arm of the clutch 60. An angular momentum applied to the number sleeve 80 along the first sense of rotation for is unalterably transferred to the clutch 60. Here, the mutually corresponding ratchet features of the ratchet mechanism 90 provide a torque transmission from the number sleeve 80 to the clutch 60.

When the desired dose has been dialed the user may simply dispense the set dose by depressing the trigger 11. This displaces the clutch 60 axially with respect to the number sleeve 80 causing dog teeth thereof to disengage. However, the clutch 60 remains keyed in rotation to the drive sleeve 30. The number sleeve 80 and the dose dial 12 are now free to rotate in accordance with the helical groove 81.

The axial movement deforms the flexible arm of the spring 40 to ensure the saw teeth cannot be overhauled during dispense. This prevents the drive sleeve 30 from rotating with respect to the housing 10 though it is still free to move axially with respect thereto. The deformation is subsequently used to urge the spring 40 and the clutch 60 back along the drive sleeve 30 to restore the connection between the clutch 60 and the number sleeve 80 when the distally directed dispensing pressure is removed from the trigger 11.

The longitudinal axial movement of the drive sleeve 30 causes the piston rod 20 to rotate through the through opening of the support of the housing 10, thereby to advance the bung 7 in the cartridge 6. Once the dialed dose has been dispensed, the number sleeve 80 is prevented from further rotation by contact of at least one stop extending from the dose dial 12 with at least one corresponding stop of the housing 10. A zero dose position may be determined by the abutment of one of axially extending edges or stops of the number sleeve 80 with at least one or several corresponding stops of the housing 10.

The expelling mechanism or drive mechanism 8 as described above is only exemplary for one of a plurality of differently configured drive mechanisms that are generally implementable in a disposable pen-injector. The drive mechanism as described above is explained in more detail e.g. in WO2004/078239A1, WO 2004/078240A1 or WO 2004/078241A1 the entirety of which being incorporated herein by reference.

The dose setting mechanism 9 as illustrated in FIG. 2 comprises at least the dose dial 12 and the number sleeve 80. As the dose dial 12 is rotated during and for setting of a dose the number sleeve 80 starts to rotate relative to the housing along a helical path as defined by the threaded engagement of its outer thread or helical groove 81 with a correspondingly shaped threaded section at the inside surface of the housing.

During dose setting and when the drive mechanism 8 or the dose setting mechanism 9 is in the dose setting mode the drive sleeve 30 rotates in unison with the dose dial 12 and with the number sleeve 80. The drive sleeve 30 is threadedly engaged with the piston rod 20, which during dose setting is stationary with regard to the housing 10. Accordingly, the drive sleeve 30 is subject to a screwing or helical motion during dose setting. The drive sleeve 30 starts to travel in proximal direction as the dose dial is rotated in a first sense or rotation or in a dose incrementing direction 4, e.g. in a clockwise direction. For adjusting of or correcting a size of a dose the dose dial 12 is rotatable in an opposite second sense of rotation, hence in a dose decrementing direction 5, e.g. counterclockwise.

Figure 3:
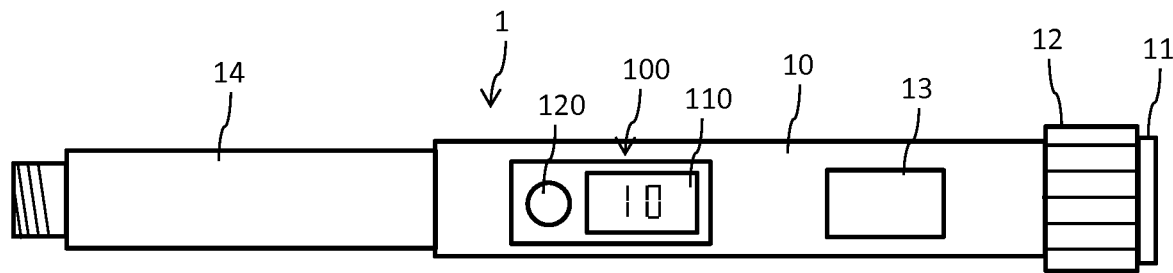
FIG. 3 shows the injection device of FIG. 1 with a touch sensitive label attached to the housing of the injection device.
Figure 5:
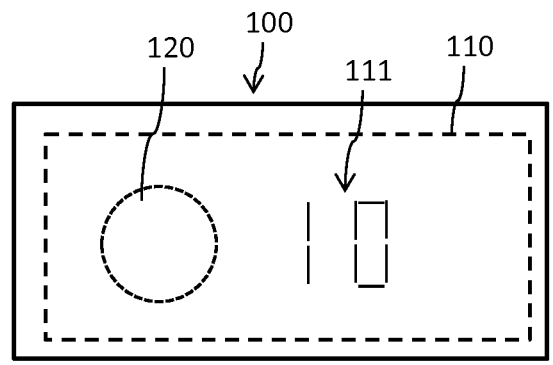
FIG. 5 shows another example of the touch sensitive label.
Figure 6:
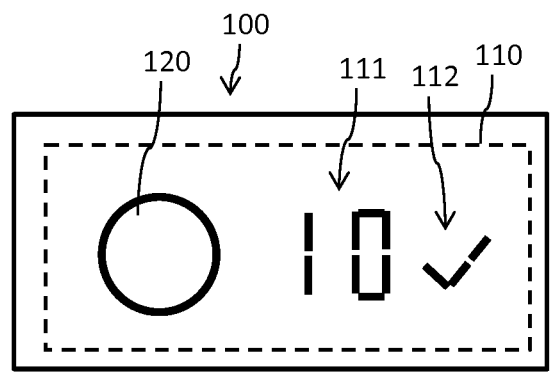
FIG. 6 shows a further example of the touch sensitive label.
Figure 7:
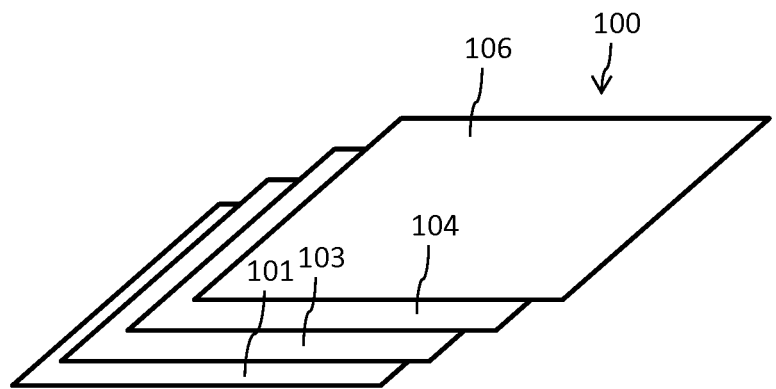
FIG. 7 shows the multilayer structure of the touch sensitive label.
Figure 8:
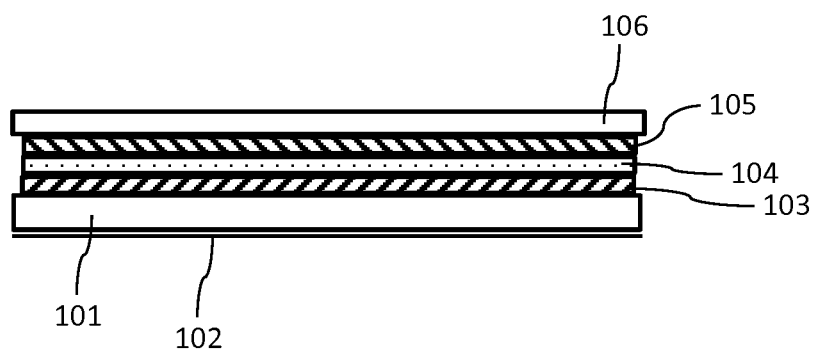
FIG. 8 is a cross-section through an example of the touch sensitive label.

In FIGS. 3-9 one example of a touch sensitive label 100 configured for attachment to the housing of the injection device 1 is illustrated. As indicated in FIG. 3 the label 100 is attachable to a sidewall of the housing 10. The touch sensitive label comprises a flexible substrate 101 as shown in FIG. 7 carrying an electronic display 110. The electronic display 110 is located on an upper side of the substrate 101. The electronic display 110 may be formed by a multilayer structure as indicated in FIGS. 7 and 8. The electronic display 110 and/or the touch sensitive label 100 may thus comprise a multilayer structure, e.g. a thin film multilayer structure.

The flexible substrate 101 is foldable or bendable around the circumference of the housing 10, which might be tubular shaped. The flexible substrate 101 and hence the entire touch sensitive label 100 may be adhesively attached to the sidewall of the housing 10 and may thus wrap around at least a portion of an outside surface of the housing 10.

The flexible substrate 101 or base substrate may be any material known for producing printed electronic labels, such as PET film or office paper. Other plastic materials are also feasible, e.g. PVC. The base substrate has an adhesive on one side to fix the label to a pen body, e.g. either permanently or removeably, depending on the choice of adhesive.

Figure 4:
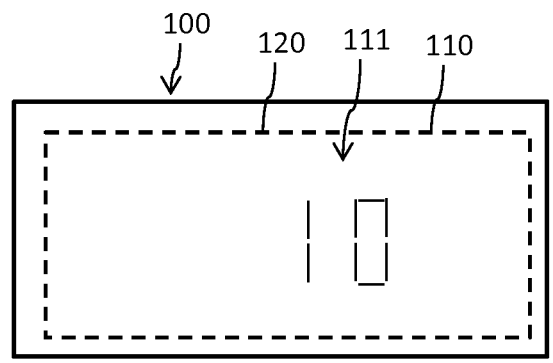
FIG. 4 is an isolated illustration of an example of the touch sensitive label.

The touch sensitive label 100 comprises an electronic display 110 and a touch sensitive area 120. In the examples of FIGS. 4-6 the touch sensitive area 120 is a dedicated area of the surface of the electronic display 110. Here, the touch sensitive area 120 is integrated into the electronic display 110. The electronic display 110 may be a touch sensitive display. The electronic display 110 is configured to visually display at least one indication 111. In the present examples the at least one indication 111 may be a number or any other symbol thus representing a size of a dose to be set and injected by the injection device 1.

The touch sensitive label 100 comprises a flexible structure. The touch sensitive label 100 is bendable or wrappable around an outer circumference of the housing 10 of the injection device 1. The electronic display 110 is a flexible display. It may comprise one of an electrophoretic display and a thin film electroluminescent display. Such displays are known to be flexible and/or bendable. They are therefore configured to become wrapped around the outer circumference of the housing 10 of the injection device 1. The display 110 is at least configured to visually illustrate the indication 111.

The touch sensitive label 100 further comprises a touch sensitive area 120. In the example of FIG. 4 the touch sensitive area 120 coincides and entirely overlaps with the electronic display 110. In another example as illustrated in FIG. 5 the touch sensitive area 120 is located inside the electronic display 110. The touch sensitive area 120 is a portion of the electronic display 110. Here, the touch sensitive area 120 is a touch sensitive part of the electronic display 110. Portions or sections of the electronic display 110 located outside the touch sensitive area 120 may be touch insensitive.

The touch sensitive area could comprise capacitive switches produced in printing electronics technology. For instance a sensor element can be designed as an electrode which is part of a capacitor. The capacitor can be "detuned" when an object, such as a finger approaches and comes in close vicinity to the capacitor. This approach has an influence on a measurable property of the capacitor, e.g. on the capacitance thereof.

In the example of FIG. 3 the touch sensitive area 120 is located outside the electronic display 110. It is located on the same side of the substrate 101. Both the touch sensitive area 120 and the electronic display 110 are located on the upper side of the substrate 101. In the example of FIG. 3 the touch sensitive area 120 may comprise a touch sensitive button or a mechanical switch. Upon touching or depressing the touch sensitive area 120, i.e. the switch, an electronic circuit 130 as for instance illustrated in FIG. 9, can be manipulated accordingly. There, the touch sensitive area 120 comprises a mechanical switch 154 configured to interrupt a connection between a battery 150 and a processor 140. In other examples the switch 154 may electrically connect or disconnect the electronic display 110 with of from the processor 140 and/or with or from the battery 150.

The touch sensitive area 120 as well as the mechanical switch 154 may be exclusively connected to the processor 140. They may be located and arranged remote from the electrical connection between the battery 150 and the processor 140.

Figure 9:
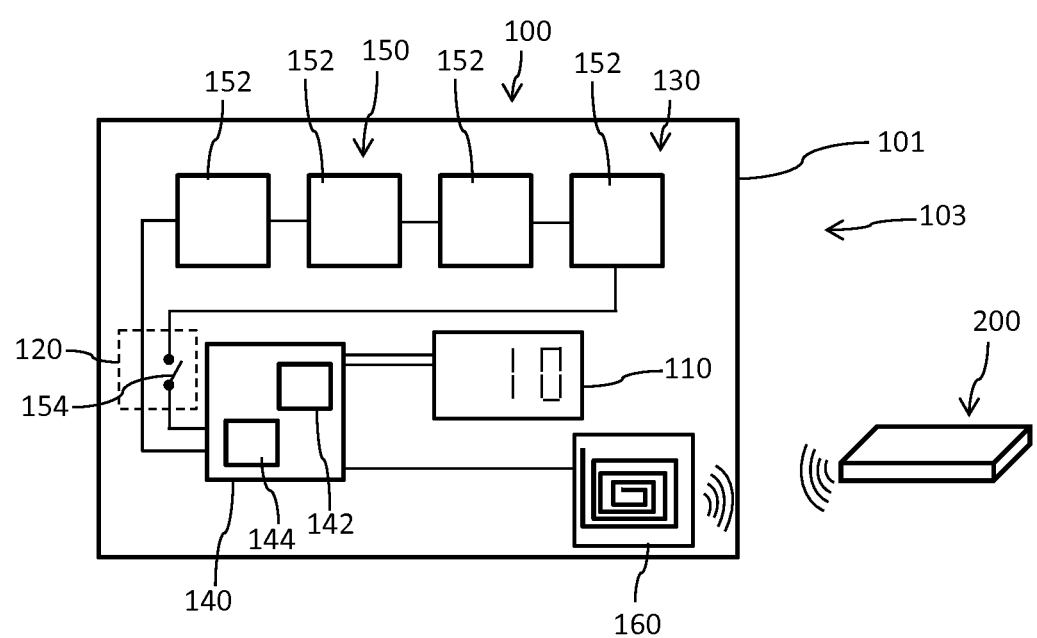
FIG. 9 is a block diagram illustrating the electronic circuit of the touch sensitive label.

The example of an electronic circuit 130 of FIG. 9 is by no way limiting for the examples of FIGS. 3-8. The electronic display 110 may superimpose the electronic circuit 130. Hence, the electronic display 110 may entirely overlap with the electronic circuit 130 located underneath. The electronic display 110 may comprise a multilayer structure as indicated in FIGS. 7 and 8. The electronic circuit 130 may be implemented in one or several of the various layers 103, 104, 105, 106 of the flexible label 100. Typically, the electronic circuit 130 is entirely provided by a conductive layer 103.

The touch sensitive area 120 may be visually indicated on the electronic display 110 or on a separate portion outside the electronic display 110. As illustrated in FIGS. 5 and 6 the touch sensitive area 120 may comprise a button shape, e.g. a circular symmetric structure. Alternatively the touch sensitive area 120 may be rectangular or of polygonal shape.

The touch sensitive area 120 is connected to the electronic display 110. The touch sensitive area 120 and the electronic display 110 are configured to interact in such a way, that upon touching or depressing of the touch sensitive area 120 the electronic display 110 changes its mode of operation. The electronic display 110 may be switchable between a default mode, e.g. illustrated in FIG. 4 and an activated mode, e.g. illustrated in FIG. 6. In the default mode the electronic display 110 may be configured to illustrate a default or predefined size of a dose by visually illustrating the at least one indication 111.

Upon touching or depressing the touch sensitive area 120 as illustrated in FIG. 5 the electronic display 110 may be configured to illustrate a confirmation 112 or other pictogram. Alternative or in addition to the illustration of the confirmation 112 the electronic display 110 may be configured to change its visual appearance. It may be configured to enhance contrast or brightness such as to indicate to a user, that the touching or depressing of the touch sensitive area 120 has been detected and recognized. When the electronic display 110 is a multicolor display it may change color in response to a touching or depressing operation of the touch sensitive area 120. Here, a background illumination of the electronic display 110 may change. Alternative, at least one of the indication 111 and/or confirmation 112 may change its color.

With other examples, the style of a visual appearance of at least one of the indication 111 and confirmation 112 may be subject to a change in response to a touching or depressing operation of the touch sensitive area 120. For instance, at least one of the indication 111 and confirmation 112 may be subject to a change with regard to brightness, font type, color, size and combinations thereof.

In additional or further alternatives, the position of the indication (e.g. dose value "10") may change on the display. E.g. upon activating the touch sensitive area the indication "10" may move from one side of the display (e.g. the left side) to the other side of the display (e.g. the right side). This change of position may indicate and prompt to a user that touching of the touch sensitive area was detected and processed.

In a further example and upon touching depressing of the touch sensitive area the processor may be configured to record a user activity and/or a point of time of a user activity in the data storage or memory of the electronic circuit. The storage may comprise capacity to store data relating to a plurality of events including time stamps, e.g. 30, 100, 1000 events.

In a further example the electronic circuit comprises an antenna providing a data transmission element, e.g. enabling NFC data transmission. This way data stored in the memory can be read out by an external device using NFC communication. NFC communication could be implemented in passive or active way, wherein the latter requires an energy source, e.g. battery, powering the electronics. The battery may be implemented in printing technology.

With an alternative example the electronic display 110 may be configured to switch off temporally so as to show a blank screen in response to the touching of the touch sensitive area 120. Even though the electronic display 110 may be switched into the activated mode by touching or depressing the touch sensitive area 120 it may provide a blank or void screen in which even the indication 111 previously illustrated during the default mode disappeared. In this activated mode the electronic display 110 may be configured to switch back or to return into the default mode after lapse of a predefined time interval. This predefined time interval may coincide or may correspond to a time interval between successive injection procedures of injection therapy. In other words as soon as the electronic display 110 returns into the default mode and visually illustrates the at least one indication 111 this is a clear indication for the user, that injection of a next dose of the medicament is currently due.

With such an example the touch sensitive label 100 is optionally equipped with a clock, e.g. implemented in a processor 140 of the electronic circuit 130. The clock basically enables counting of a predefined time interval, thus the time interval between two consecutive touching instances of the touch sensitive area 120.

The processor 140 and the electronic display 110 may be further configured to automatically switch from a default mode into an alert mode, e.g. when setting and injecting of a next dose should be overdue. In the alert mode the electronic display 110 may provide enhanced contrast and/or enhanced brightness compared to the default mode. In addition and in the alert mode the processor 140 and the electronic display 110 may be configured to visualize an alert signal thus indicating to the user, that setting and injecting of the proceeding dose of the medicament is currently overdue. In the alert mode, the electronic display 110 may be subject to a regular change of its visual appearance. It may regularly or irregularly modify at least one of the following parameters: brightness, contrast, color. Moreover, the at least one indication 111 answers or confirmation 112 may be subject to a regular or irregular modification. In the aloes mode, the electronic display 110 may provide a blinking or flickering effect thus attracting the user's attention.

FIG. 9 shows one example of an electronic circuit 130 of the touch sensitive label 100. The electronic circuit 130 may be directly printed on the flexible substrate 101. The electronic structures and/or the conductive structures of the electronic circuit 130 might be bendable or flexible as well. The integrity or functionality of the electronic circuit 130 is substantially unaffected by a bending or flexing of the flexible substrate 101 and/or of the electronic circuit 130.

The electronic circuit 130 comprises a battery 150 typically equipped with numerous battery cells 152. The individual battery cells 152 are electrically connected. They may be connected in series or parallel depending on the voltage provided by the individual battery cells 152 and depending on the voltage required by the processor 140. The battery 150 and/or its battery cells 152 may comprise a printed electronic structure. Hence, the battery 150 and/or the battery cells 152 our printed batteries or battery cells and may be arranged on the substrate 101 by way of printing.

The processor 140 is connected to the battery 150 as well as to the electronic display 110. The interconnection between the battery 150 and the processor 140 may be interrupted by the switch 154 located in the touch sensitive area 120. Depressing of the switch 154 may either connect or disconnect the electrical connection between the battery 150 and the processor 140. The processor 140 is further connected to the electronic display 110. The graphical representation on the electronic display 110, e.g. various display segments or pixels of the electronic display 110 may be individually activated or deactivated by the processor 140.

The processor 140 comprises a central processing unit (CPU) 142 and a storage 144. In the storage numerous predefined indications 111 may be stored, which upon registration of a closing or opening of the switch 154 might be illustrated on the electronic display 110. When equipped with a data storage 144 the processor 140 may be further configured to count a number of touch operations of the touch sensitive area 120. Every time a user uses the injection device 1 and depresses or touches the touch sensitive area 120 this touching or depression may be registered and counted in the storage 144. If the processor 140 is further equipped with a clock every touch instant can be further assigned with a timestamp thus allowing to record a dosing history or to record the points in time at which the touch sensitive area 120 was appropriately touched by the user of the injection device 1.

Even though the touch sensitive area 120 is illustrated offset or remote from the electronic display 110 in FIG. 9 there might be examples wherein the electronic display 110 overlaps with the touch sensitive area 120 or wherein the entire electronic display 110 is touch sensitive. With such examples the touch sensitive area 120 and the electronic display 110 may entirely or at least partially overlap.

The electronic circuit 130 may further comprise an antenna 160 connected to the processor 140. The antenna 160 may be configured for wireless data transmission. The antenna 160 may be configured as a receiving antenna and/or as a broadcasting antenna. The antenna 160 may be configured to transmit electromagnetic signals in the RF frequency band. The antenna 160 may comprise an RFID antenna. The antenna 160 may be configured in accordance to conventional wireless communication standards, such as Bluetooth, NFC or IEEE 802.11 (WLAN). The antenna 160 is configured to exchange data with an external electronic device 200, such as a smart watch, a smartphone, a tablet computer or a personal computer.

The processor 140 may be reconfigurable by signals obtained from the external electronic device 200 via the antenna 160. In this way the external electronic device 200 can be used to modify or to reconfigure the processor 140 and hence to modify and to reconfigure the content of the electronic display 110. In addition or alternative the external electronic device 200 may be further configured to read out the data storage 144 of the electronic circuit 130. In this way the dosing history and the use of the touch sensitive label 100 can be precisely monitored and transmitted to the external electronic device 200 for further processing and/or evaluation.

The entirety of the electronic components of the electronic circuit 130, e.g. the wired connections between the battery 150 and the battery cells 152, the switch 154 or the touch sensitive area 120, the antenna 160 as well as the processor 140 may comprise or may be formed by a printing process on the substrate 101. In this way a separate assembly and arrangement of numerous electronic components on the substrate 101 becomes substantially superfluous. This enables a cost efficient mass manufacturing of the touch sensitive label 100.

A lower side of the substrate 101 may be provided with an adhesive. The adhesive may be provided on an adhesive layer 102 entirely or at least partially covering the lower side of the substrate 101 located opposite to the conductive layer 103 on which the electronic circuit 130 is located. In FIG. 8 a stack of numerous layers 103, 104, 105, 106 configured to form the electronic display 110 is exemplary illustrated. The stack structure of FIG. 8 represents a thin film electroluminescent display 110. The substrate 101 may be pliable and may comprise or consist of one of the following: foldable office paper, transparent or non-transparent PET film, leather, wood, ceramics, and a metal foil. The electroluminescent display is configured to actively emit light.

A segment of the display consists of two overlaid electrodes that act as a capacitor. The oppositely located electrodes are provided in the conductive layer 103 and in the transparent electrode layer 106. Between these layers 103, 106 there is provided a dielectric layer 104 and an electroluminescent layer 105, e.g. in form of a phosphor layer. If a suitable voltage and a suitable current AC signal is applied the electroluminescent layer 105 emits photons.

The stack of layers 103, 104, 105, 106 may add only 100-150 μm of thickness to the substrate 101. In this way the electronic display 110 can be extraordinarily thin.

With other examples the flexible electronic display 110 is implemented as an electrophoretic display that is based on rearranging charged pigment particles by means of an applied electric field. There, titanium dioxide particles of appropriately 1 μm in diameter may be dispersed in a hydrocarbon oil. A dark colored dye is added to the oil along with surfactants and charging agents that cause the particles to take on an electric charge. This mixture is placed between two parallel, conductive plates separated by a gap of 10-100 μm. When a voltage is applied across the two plates the particles migrate electrophoretically to the plate that bears the opposite charge from that on the particles.

When the particles are located at the front or a viewing side of the display, it appears white because light is scattered back to the viewer by the high index titania particles. When the particles are located at the rear side of the display it appears dark because the incident light is absorbed by the colored dye. If the rear electrode is divided into a number of small picture elements or pixels, an image can be formed by applying the appropriate voltage to each region of the display to create a pattern of reflecting and absorbing regions. Electrophoretic displays are considered prime examples of an electronic paper category because of their paperlike appearance and lower power consumption.

The touch sensitive label 100 may only be optionally equipped with an antenna 160. With one implementation the label 100 may be void of an antenna 160 and may be operable to illustrate a well-defined or predefined indication 111 and to provide a switching between the default mode, the activated mode and/or the alert mode, e.g. in response to the touching or depressing of the touch sensitive area 120.

Figure 10:
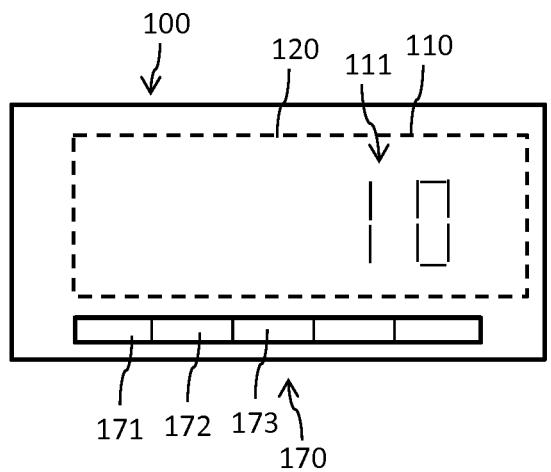
FIG. 10 shows another example of the touch sensitive label equipped with a sensor.
Figure 11:
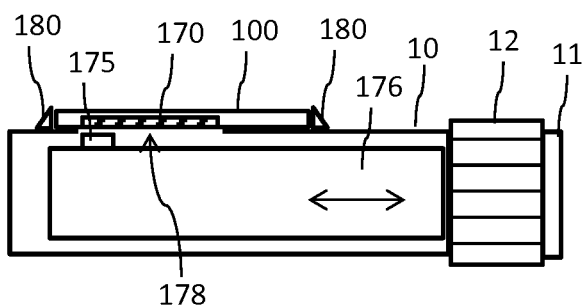
FIG. 11 shows a cross-section through the injection device with the touch sensitive label attached thereto.
Figure 12:
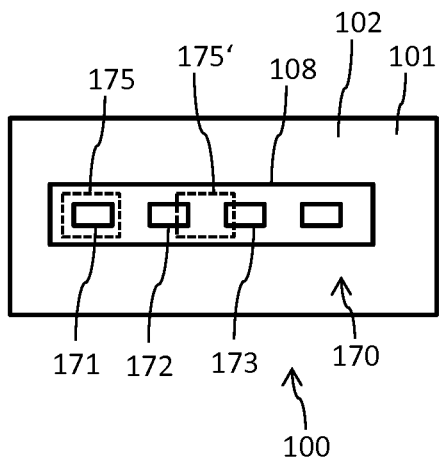
FIG. 12 shows a lower side of one example of the touch sensitive label of FIG. 10.

In FIGS. 10-12 there is illustrated a further example of the touch sensitive label 100. This label 100 may be implemented with or without an antenna 160. It comprises a flexible substrate 101 with the electronic display 110 and the touch sensitive area 120. Typically, the label 100 of FIG. also comprises a processor 140, a CPU 142, a data storage 144 and a battery 150 as described above in connection with FIG. 9. In addition to the examples as described above in connection with FIGS. 3-9 the label 100 of FIGS. 10-12 further comprises a sensor 170.

The sensor 170 is configured to allocate or to determine a position and/or a rotational state of at least one of a dose tracker 176 and a preselector 95 of the injection device 1 when the label 100 is attached to the housing 10 in a predefined manner. For this the housing 10 may comprise at least one or several position marks 180 illustrated in FIG. 11 as protrusions on the outside surface of the housing 10. The label 100 has to be properly attached to the housing 10 in the area as defined by the at least one or several position marks 180. The dose tracker 176 may coincide with the number sleeve 80 of the injection device 1 or may be formed by the number sleeve. The dose tracker 176 comprises an indicator 175 whose positional state, i.e. the longitudinal position and/or a rotational orientation relative to the housing 10 is detectable by the sensor 170.

The preselector 95 schematically illustrated in FIG. 2 may be one of slidably or rotationally movable relative to the housing 10. It may be slidably or rotationally connected to the sidewall of the housing 10. The preselector 95 is movable between at least two discrete positional states, each of which defining and limiting a path length along which the dose tracker 176 is displaceable during setting of a dose. The preselector 95 is at least one of longitudinally or rotationally displaceable between a first stop position and a second stop position. Each stop position it is at least releasably fixable to the housing. The preselector 95 typically comprises a preselector stop feature to engage with a correspondingly shaped tracking stop feature of the dose tracker 176. The dose tracker 176 is displaceable in a dose incrementing direction until tracking stop feature engages the preselector stop feature. A further rotation or movement of the dose tracker beyond this engagement position is hindered and blocked by the preselector 95.

In the presently illustrated examples only the dose tracker 176 comprises an indicator 175 whose position is detectable by the sensor 170. The preselector 95 may be equally equipped with the indicator 175 configured to interact with the sensor 170. With one example of the touch sensitive label 100 only the preselector 95 is equipped with the indicator 175 and the dose tracker 176 is void of the indicator 175.

With other examples both, the preselector 95 and the indicator dose tracker 176 are each equipped with an own indicator 175. The indicator of the dose tracker 176 may distinguish from the indicator of the preselector 95. The sensor 170 may be configured to distinguish between the indicator of the dose tracker 176 and the indicator of the preselector 95. The sensor 170 and/or the processor 140 may be thus configured to determine both, a positional state of the dose tracker 176 and the preselector 95.

The position mark 180 may protrude from the sidewall of the housing 10 or may comprise a recess in the housing 10. Alternative, the position mark 180 may be void of protrusions or recesses in the outside surface of the housing 10. The position mark 180 may simply comprise a visual indication, such as a border region inside which the label 100 should be adhesively attached.

In one example the sensor 170 comprises numerous discrete sensor segments 171, 172, 173 that are separated along a moving direction of the indicator 175 and/or of the dose tracker 176 relative to the housing 10. As the dose tracker 176 is subject to a rotational and/or sliding movement relative to the housing 10 the indicator 175, e.g. initially overlapping with a first sensor segment 171 moves towards a second sensor segment 172 and, e.g. further towards the third sensor segment 173. The movement of the indicator 175 relative to the numerous sensor segments 171, 172, 173 is detectable by the sensor 170 that is electrically connected to the processor 140. In this way, the processor 140 and the sensor 170 are configured to determine and to detect an actual position and/or rotational state of the indicator 175 and hence of the dose tracker 176 relative to the housing 10.

The position or rotational state of the dose tracker 176 unequivocally coincides with a size of a dose actually set by the injection device 1. In this way, the processor 140 may be configured to determine or to measure a size of a dose actually set with the injection device 1 when the label 100 is appropriately connected to the housing 10. The determined longitudinal or rotational position of the dose tracker may be thus compared with a predefined position, e.g. indicated by the indication 111 on the electronic display 110. The dose actually set with the injection device may be further illustrated through the dosage window 13.

The processor 140 and the electronic display 110 may be further configured to generate at least one of a visual indication 111 and a visual confirmation 112 on the electronic display 110 if the determined longitudinal or rotational position of the dose tracker 176 matches with a predefined position. Alternatively or additionally the processor may be configured to generate at least one of a visual indication 111 and a visual confirmation 112 on the electronic display 110 if the determined longitudinal or rotational position of the dose tracker 176 does not match with the predefined position.

Typically and as long as the determined longitudinal or rotational position of the dose tracker actually measured by the sensor 120 does not match with a predefined position or with a predefined size of a dose the processor is configured to generate a visual indication on the electronic display thus indicating to a user, that the size of the dose actually set is too large or too small. For this the electronic display 110 may be configured to generate a respective indication 111, e.g. in form of an arrow pointing into the respective direction along which the dose dial 12 has to be rotated until the size of the dose actually set and determined by the sensor 170 matches with a predefined size of a dose.

Alternative to the generation of dose size indicating symbols it is also conceivable that the electronic display 110 changes its visual appearance, e.g. in form of an abrupt enhancement of contrast and/or brightness. If the electronic display 110 is a multicolored display it may also change color when, e.g. a dose size actually measured matches with a predefined dose that should be set and injected by the injection device 1.

The specific implementation of the sensor 170 and the indicator 175 may vary. As illustrated in FIG. 11 the housing 10 may comprise a through opening 178 or a recess through which the position of the indicator 175 can be for instance mechanically or electrically detected, e.g. by means of numerous contact pins provided on each sensor segment 171, 172, 173. For this, there may be established a direct mechanical contact between the indicator 175 and at least one of the sensor segments 171, 172, 173. As schematically illustrated in FIG. 12 the lower side of the substrate 101 comprises a recess 108 through which the sensor segments 171, 172, 173 are accessible or through which the sensor segments 171, 172, 173 may reach.

Alternatively, the sensor segments 171, 172, 173 may slightly protrude from the lower side of the substrate 101 so as to reach through or into the through opening 178 or recess of the housing 10. If appropriately attached to the housing 10 the sensor segment 171 may be in electrical contact with the indicator 175 as shown in FIG. 12. The electrical contact between the sensor segment 171 and the indicator 175 may be detected by the sensor 170 and/or by the processor 140.

As the indicator 175 and the dose tracker is subject to a movement, e.g. along the longitudinal direction of the recess 108 it may move away from the first sensor segment 171 and may slide or rotate past the second sensor segment 172. As further illustrated in FIG. 12 and when moved away from an initial position the indicator 175' may be located between the second sensor segment 172 and a third sensor segment 173. There it may be in contact with both sensor segments 172, 173. This position may be detected by both of the segments 172, 173.

With other examples the indicator 175 may be magnetically encoded and the sensor segments 171, 172, 173 may be configured to detect a magnetic field of the indicator 175 as the indicator 175 is subject to a longitudinal and/or rotational movement. With a further example the indicator 175 and the sensor segments 171, 172, 173 may be implemented electrostatically. Here, the numerous sensor segments 171, 172, 173 may be configured to allocate or to detect a modification of an electric field induced by the indicator 175. Furthermore, the sensor segments 171, 172, 173 may comprise capacity measuring elements configured to measure a modification of an electric field or electric capacitance in the vicinity of the respective sensor segments 171, 172, 173. Magnetic, electrostatic and capacitive measurement procedures may be of particular benefit because they may not require a through opening 178 or recess in the sidewall of the housing 10. With such implementations the label 100 may be simply adhesively attached within the given position marks on the outside surface of the housing 10.

Figure 13:
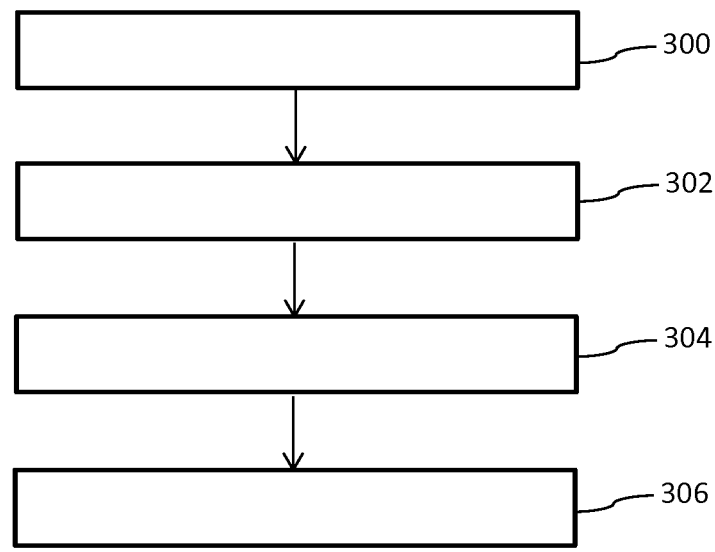
FIG. 13 shows a flowchart representing various steps of using the touch sensitive label.

In FIG. 13 a flowchart is illustrative of a method of using the touch sensitive label. In a first step 300 the label 100 is attached to the injection device 1. The label 100 is typically attached to a sidewall 10 of the injection device 1. For this, a release sheet covering an adhesive layer 102 on the lower side of the substrate 101 is removed so to expose the adhesive layer 102. The substrate 101 and the entire label 100 may thus be folded around or wrapped around the sidewall of the housing 10, typically within a position mark 180.

After attaching the label to the injection device in step 300 a user may touch or depress the touch sensitive area 120 in step 302 to switch the label 100 form the default mode into the activated mode. In response to the touching or depression of the touch sensitive area 120 in step 302 in a following step 304 the label 100 actually switches from one of the default mode and the activated mode into the other one of the default mode at the activated mode. In effect, the electronic display 110 modifies its visual appearance. Optionally and in a further step 306 the electronic display 110 may return into the default mode when switched in the preceding step 304 from the default mode into the activated mode. Returning into the default mode in step 306 may be triggered autonomously by the processor 140 after lapse of a predefined time interval.

Reference Numbers 1 injection device
2 distal direction
3 proximal direction
4 dose incrementing direction
5 dose decrementing direction
6 cartridge
7 bung
8 drive mechanism
9 dose setting mechanism
10 housing 11 trigger
12 dose dial
13 dosage window
14 cartridge holder
15 injection needle
16 inner needle cap
17 outer needle cap
18 protective cap
19 protrusion
20 piston rod
21 bearing
22 first thread
23 pressure foot
24 second thread
25 barrel
26 seal
28 threaded socket
30 drive sleeve
31 threaded section
32 flange
33 flange
35 last dose limiter
36 shoulder
40 spring
41 recess
50 dose tracker
51 tracking stop feature
60 clutch
62 insert piece
64 stem
80 number sleeve
81 groove
90 ratchet mechanism
91 ratchet feature
95 preselector
100 label
101 substrate
102 adhesive layer
103 conductive layer
104 dielectric layer
105 electroluminescent layer
106 transparent electrode layer
108 recess
110 electronic display
111 indication
112 confirmation
120 touch sensitive area
130 electronic circuit
140 processor
142 CPU
144 data storage
150 battery
152 battery cell
154 switch
160 antenna
170 sensor
171 sensor segment
172 sensor segment
173 sensor segment
175 indicator
176 dose tracker
178 through opening
180 position mark
200 external electronic device

The invention claimed is:

1. A touch sensitive label to be attached on an injection device, the label comprising:
a flexible substrate configured to be attached to a housing of the injection device;
an electronic display located on the substrate and configured to visually display at least one indication;
a touch sensitive area located on the substrate and electrically connectable to the electronic display; and
a processor connected to the electronic display and configured to modify a visual appearance of the at least one indication in response to a user touching or depressing the touch sensitive area.

2. The label according to claim 1, wherein the touch sensitive area is located outside the electronic display.

3. The label according to claim 1, wherein one or more portions of a lower side of the flexible substrate comprises an adhesive.

4. The label according to claim 1, wherein the electronic display is one of an electrophoretic display or a thin-film electroluminescent display.

5. The label according to claim 1, further comprising an electronic circuit located on the substrate and electrically connected to the touch sensitive area, to the electronic display, and to the processor.

6. The label according to claim 5, wherein the electronic circuit comprises a battery.

7. The label according to claim 5, wherein the electronic circuit comprises a data storage device configured to store at least one of a number of user activities or a point of time of a user activity.

8. The label according to claim 5, wherein the electronic circuit comprises an antenna for wirelessly transmitting electronic signals to an external electronic device.

9. The label according to claim 5, wherein the electronic circuit comprises a sensor configured to determine at least one of a position or a rotational state of at least one of a dose tracker or a preselector of the injection device when the label is attached to the injection device.

10. The label according to claim 9, wherein the sensor comprises at least a first sensor segment and a second sensor segment arranged at a predefined distance from each other, wherein each of the first sensor segment and the second sensor segment is configured to detect a presence or a position of an indicator of one of the dose tracker or the preselector.

11. The label according to claim 9, wherein the processor is configured to generate at least one of a visual indication or a visual confirmation on the electronic display in response to determining a matching or a non-matching of (i) a longitudinal or a rotational position of the dose tracker with (ii) a predefined position.

12. The label according to claim 5, wherein the electronic circuit comprises at least one printed electronic component.

13. The label according to claim 1, wherein the touch sensitive area is integrated into the electronic display.

14. An injection device for setting and injecting of a dose of a medicament, the injection device comprising:
a housing configured to accommodate a medicament container;
a drive mechanism configured to withdraw or to expel the dose of the medicament from the medicament container and configured to inject the dose of the medicament into biological tissue; and a touch sensitive label attached to the housing, the touch sensitive label comprising:
a flexible substrate configured to be attached to the housing of the injection device;
an electronic display located on the substrate and configured to visually display at least one indication,
a touch sensitive area located on the substrate and electrically connectable to the electronic display, and
a processor connected to the electronic display and configured to modify a visual appearance of the at least one indication in response to a user touching or depressing the touch sensitive area.

15. The injection device according to claim 14 further comprising the medicament container arranged inside the housing.

16. The injection device according to claim 14, further comprising an electronic circuit located on the substrate and electrically connected to the touch sensitive area, to the electronic display, and to the processor,
wherein the electronic circuit comprises a data storage device configured to store activity data indicating at least one of a number of user activities or a point of time of a user activity.

17. The injection device according to claim 16, wherein the activity data is stored in the data storage in response to the user touching or depressing the touch sensitive area.

18. The injection device according to claim 16, wherein the electronic circuit further comprises an antenna for wirelessly transmitting electronic signals to an external electronic device.

19. The injection device according to claim 16, wherein the electronic circuit further comprises a sensor configured to determine at least one of a position or a rotational state of at least one of a dose tracker or a preselector of the injection device.

20. The injection device according to claim 19, wherein the sensor comprises at least a first sensor segment and a second sensor segment arranged at a predefined distance from each other, wherein each of the first sensor segment and the second sensor segment is configured to detect a presence or a position of an indicator of one of the dose tracker or the preselector.

* * * * *